BEST AVAILABLE COPY

United States Patent [19]

Urline

[11] Plant 4,814

[45] Jan. 26, 1982

[54] ALMOND TREE

[75] Inventor: Fred B. Urline, Winton, Calif.

[73] Assignees: Jenette P. Thurman; Karen K. Howe; Susan A. Bizzack; Richard D. Urline; Sharon D. Williams, all of Winton, Calif.

[21] Appl. No.: 211,060

[22] Filed: Nov. 28, 1980

[51] Int. Cl.[3] ..... A01H 5/03

[52] U.S. Cl. ..... Plt./30

[58] Field of Search ..... Plt./30

*Primary Examiner*—Robert E. Bagwill

*Attorney, Agent, or Firm*—Roger B. Webster

[57] ABSTRACT

An almond tree which is of medium size, dense, vigorous, upright with strong branches, abundantly foliated with medium size, lanceolate leaves having a finely serrate margin, and alternate, medium size, globose glands, blooms white and very heavily substantially with the Nonpareil, and is a regular and very heavy bearer of small, well-distributed nuts borne essentially in clusters on short spurs and in harvest after the Nonpareil but before the Mission, and the nuts having small kernels.

1 Drawing Figure

BACKGROUND OF THE VARIETY

Field of the Invention

In the course of the maintenance of an almond orchard on my ranch located near Winton, Merced County, Calif., I frequent such orchard for the purpose of inspection, cultivation, and irrigation, and—during the course of such activities—I am aware of the condition of the trees and recognize any other-than-normal growth characteristics of them. It was under such conditions that the present variety of almond tree was discovered by me.

Classification of the Variety

The present new and distinct variety of almond tree is embraced by Class 30, Plants, of the U.S. Patent Office Manual of Classification.

Prior Varieties

Among the existent varieties of almond tree which are know to me, and mentioned herein, are Nonpareil (unpatented), Mission (unpatented), and Merced (U.S. Plant Pat. No. 1,730).

ORIGIN OF THE VARIETY

The present variety of almond tree was discovered by me in an area of my ranch near the almond orchard, located as aforesaid, as one of two tree trunks—of a chance seedling—emergent from the ground. Upon close and continued observation of such one tree trunk, I confirmed my initial realization that it, and its crop, had certain novel and distinctive characteristics in comparison to the other tree trunk and known varieties such as the Nonpareil, Mission, and Merced. I, therefore, determined to effect asexual reproduction of the variety, and potentially for commercial growing.

ASEXUAL REPRODUCTION OF THE VARIETY

The present variety of almond tree was asexually reproduced by me, by budding, on my ranch located as aforesaid; such reproductions having been successful and, in maturity, ran true in all respects to said one trunk of such chance seedling.

SUMMARY OF THE VARIETY

The herein-claimed variety of almond tree is—characteristically—of medium size, dense, vigorous, upright with strong branches, abundantly foliated with medium size, lanceolate leaves having a finely serrate margin, and alternate, medium size, globose glands, blooms white and very heavily substantially with the Nonpareil, and is a regular and very heavy bearer of small, well-distributed nuts borne essentially in clusters on short spurs and in harvest after the Nonpareil but before the Mission, and the nuts having small kernels.

The herein-claimed variety of almond tree is further, and particularly, characterized as follows:

The tree, which grows upright with strong branches, resembles the Mission in shape but is larger.

The tree blooms substantially with and is a pollenizer for the Nonpareil, while the nuts—which are small—harvest after the Nonpareil but before the Merced; the tree bearing heavily, including seasons when the Nonpareil has a relatively small crop.

The nuts have hulls which split not only along the suture, but in many instances transversely intermediate the base and apex.

The nuts are substantially free of gum.

BRIEF DESCRIPTION OF THE DRAWING

The drawing is an illustration, by photographic reproduction in color, of a twig with leaves and nuts in hull and—separately—nuts in hull, nuts out of hull, and kernels out of shell.

DESCRIPTION OF THE VARIETY

The botanical details of this new and distinct variety of almond tree—with color definitions (except those in common color terms) referenced to Maerz and Paul Dictionary of Color (First Edition)—are as follows:

Tree:
- *Density.*—Dense.
- *Size.*—Medium.
- *Vigor.*—Vigorous.

Trunk:
- *Form.*—Medium.
- *Texture.*—Medium.

BEST AVAILABLE COPY

Branches:
*Form.*—Stocky.
*Texture.*—Smooth.
*Lenticels.*—Numerous. Medium size.
*Branching habit.*—Upright, with strong branches.
*Color.*—New wood: green. Mature wood: dull brown.

Foliage:
*Quantity.*—Abundant.

Leaves:
*Size.*—Medium. Average length — 3¼". Average width — ¾".
*Shape.*—Lanceolate.
*Thickness.*—Medium.
*Texture.*—Smooth.
*Margin.*—Finely serrate.
*Petiole.*—Long. Average length — ⅞".
*Glands.*—Average number — 4. Alternate. Medium size. Globose. Green. Positioned on petiole.
*Stipules.*—Present.
*Color.*—Top side — dark green (23-L-8). Under side — lighter green (22-L-8).

Bloom:
*Amount of bloom.*—Very heavy.
*Color.*—White.
*Blooming period.*—Medium. Substantially with Nonpareil.

Crop:
*Bearing.*—Regular bearer.
*Productivity.*—Very heavy.
*Distirubtion of nuts on tree.*—In clusters on short spurs.
*Harvest period.*—Following Nonpareil and before Merced.
*Tenacity.*—Hangs well on tree. Easy to harvest. Easy to hull.

Hull:
*Outer surface.*—Smooth.
*Form.*—Regular.
*Thickness.*—Thin.
*Flesh.*—Tough.
*Suture.*—Ridged.
*Color.*—Light green (21-J-5) with a silvery sheen.
*Pubescence.*—Medium.
*Dehiscence.*—Opens freely.
*Splitting.*—Along suture, and — in many instances — transversely intermediate the base and apex. Freely at base.

Nut:

*Size.*—Small. Average length — 1¼". Average width — ¾". Average thickness — ½". Average weight — 15 per ounce.
*Form.*—Length/width: ovate. Width/thickness: plump.
*Shell.*—Soft. Outer shell: hard. Crumbling. Inner shell: soft. Well sealed.
*Color.*—Light brown (14-L-9).
*Pits.*—Small.
*Base.*—Ventrally oblique.
*Stem scar.*—Small.
*Apex.*—Acuminate. Sharp.
*Wing.*—Thin.
*Inner surface.*—Light colored.
*Ventral streak.*—Light colored. Narrow.
*Percentage of kernel to nut.*—67%.
*Gum.*—Nuts substantially free of gum.

Kernel:
*Size.*—Small. Average length — 13/16". Average width — 9/16". Average thickness — ⅜". Average weight — 22 per ounce.
*Form.*—Length/width: ovate. Width/thickness: plump.
*Base.*—Ventrally oblique.
*Stem scar.*—Small.
*Apex.*—Acuminate. Sharp.
*Texture.*—Wrinkled.
*Pellicle.*—Thin.
*Pubescence.*—Medium.
*Color.*—Buckthorn brown (13-L-8).
*Number of doubles.*—Few.
*Defective kernels.*—No particular defects noted.
*Flavor.*—Sweet.
*Quality.*—Very good.

Resistance to insects and diseases: No more susceptible than any commercial variety under same growing conditions.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, particularly characterized by a tree which resembles the Mission in shape but is larger; and by blooming substantially with and pollenizing the Nonpareil, but in harvest after the Nonpareil and before the Merced.

* * * * *

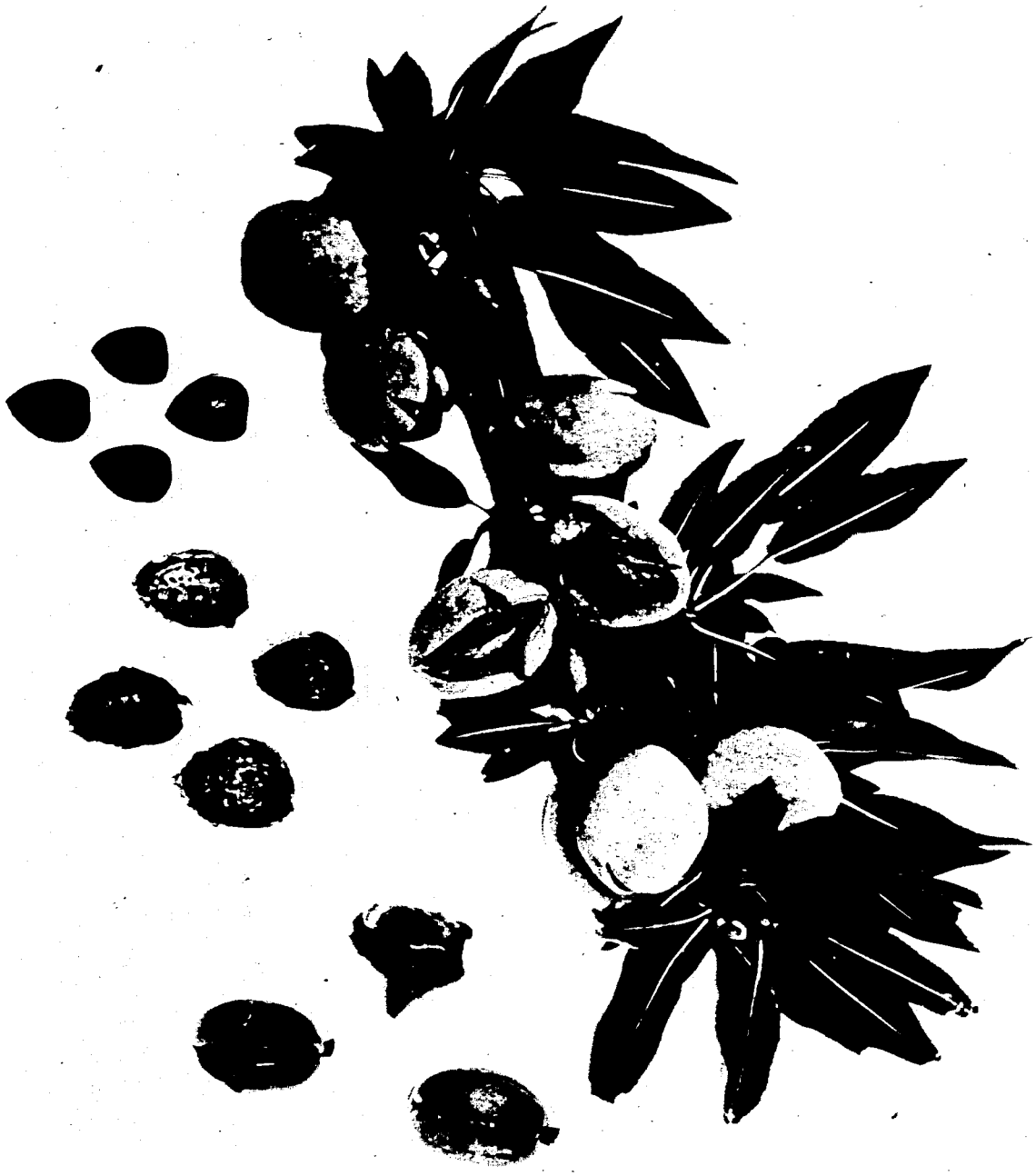

H9398 OR PP 4,814
BEST AVAILABLE COPY